(12) United States Patent
Miyazaki (10) Patent No.: US 12,373,921 B2
(45) Date of Patent: Jul. 29, 2025

(54) IMAGE PROCESSING APPARATUS AND RECORDING MEDIUM

(71) Applicant: Konica Minolta, Inc., Tokyo (JP)

(72) Inventor: Haruhiko Miyazaki, Toyohashi (JP)

(73) Assignee: KONICA MINOLTA, INC., Tokyo (JP)

( * ) Notice: Subject to any disclaimer, the term of this patent is extended or adjusted under 35 U.S.C. 154(b) by 308 days.

(21) Appl. No.: 17/837,450

(22) Filed: Jun. 10, 2022

(65) Prior Publication Data

US 2022/0395245 A1 Dec. 15, 2022

(30) Foreign Application Priority Data

Jun. 14, 2021 (JP) ................. 2021-098460

(51) Int. Cl.
*G06T 5/50* (2006.01)
*A61B 6/00* (2006.01)

(52) U.S. Cl.
CPC .............. *G06T 5/50* (2013.01); *A61B 6/5258* (2013.01); *A61B 6/487* (2013.01); *A61B 6/5235* (2013.01); *G06T 2207/10116* (2013.01); *G06T 2207/30168* (2013.01)

(58) Field of Classification Search
CPC ............. G06T 5/50; G06T 2207/10116; G06T 2207/30168; A61B 6/5235; A61B 6/486
See application file for complete search history.

(56) References Cited

U.S. PATENT DOCUMENTS 8,594,274 B2 * 11/2013 Hoernig ................. A61B 6/502
382/128
10,219,769 B2 * 3/2019 Fukuda ................. G06T 7/0012

11,354,831 B2 * 6/2022 Feng ...................... A61B 6/504
2008/0095422 A1 4/2008 Suri et al.
2017/0278244 A1 9/2017 Luo et al.

FOREIGN PATENT DOCUMENTS

| JP | 2007082907 A | 4/2007 |
| JP | 2014050417 A | 3/2014 |
| JP | 2019063328 A | 4/2019 |
| JP | 2019212138 A | 12/2019 |

OTHER PUBLICATIONS

JPO Notice of Reasons for Refusal for corresponding JP Application No. 2021-098460; Issued Jan. 7, 2025.

* cited by examiner

*Primary Examiner* — Phuoc Tran
(74) *Attorney, Agent, or Firm* — CANTOR COLBURN LLP (57) ABSTRACT

An image processing apparatus processes a kinetic image obtained by kymography of irradiating a subject with radiation to photograph a moving state of the subject. The image processing apparatus includes an acquisition unit, a generator, and an output controller. The acquisition unit acquires a plurality of frame images constituting the kinetic image. The generator generates a first image which is a synthesized still image obtained by synthesizing at least two or more frame images among the plurality of frame images. The output controller that outputs the first image to an output unit. Before generating the first image, the output controller outputs a second image which is a still image based on at least one or more frame images among the plurality of frame images and has an image quality lower than an image quality of the first image.

11 Claims, 5 Drawing Sheets

IMAGE PROCESSING APPARATUS AND RECORDING MEDIUM

CROSS-REFERENCE TO RELATED APPLICATION

The present invention claims priority under 35 U.S.C. § 119 to Japanese Patent Application No. 2021-098460, filed on Jun. 14, 2021, the entire contents of which are incorporated herein by reference.

BACKGROUND

1. Technological Field

The present invention relates to an image processing apparatus and a recording medium.

2. Description of the Related Art

A conventionally known technology synthesizes a plurality of frame images constituting a kinetic image to generate a single synthesized still image. For example, JP 2019-212138 A describes generating a synthesized still image automatically increased in resolution without a user designating a reference frame image when generating the synthesized still image increased in resolution among a plurality of frame images constituting a kinetic image.

However, the technology described in JP 2019-212138 A enables a user to confirm content of the synthesized still image only after a synthesized still image generation process is completely finished and the synthesized still image is displayed. Thus, in a case in which a processing time from when the synthesized still image generation process is started to when the synthesized still image is displayed is long, the waiting time of the user is also prolonged, and the user feels temporal stress. Moreover, until the synthesized still image is displayed, the user is not able to confirm a progress state as to whether the synthesized still image generation process is being executed normally. Furthermore, in a case in which even if the synthesized still image is displayed, an automatically selected reference frame image is an inappropriate image for a reason such as not having user desired content, for example, reprocessing or rephotographing is required. As a consequence, the waiting time required for generating the synthesized still image is wasted.

SUMMARY

The present invention has an object to reduce stress on a user and a wasted waiting time when generating a synthesized still image from a plurality of frame images constituting a kinetic image.

To achieve at least one of the above-mentioned objects, according to an aspect of the present invention, an image processing apparatus processes a kinetic image obtained by kymography of irradiating a subject with radiation to photograph a moving state of the subject. The image processing apparatus includes: an acquisition unit that acquires a plurality of frame images constituting the kinetic image; a generator that generates a first image which is a synthesized still image obtained by synthesizing at least two or more frame images among the plurality of frame images; and an output controller that outputs the first image to an output unit. Before generating the first image, the output controller outputs a second image which is a still image based on at least one or more frame images among the plurality of frame images and has an image quality lower than an image quality of the first image.

According to another aspect of the present invention, a non-transitory recording medium has stored thereon a program for a computer to be used in an image processing apparatus that processes a kinetic image obtained by kymography of irradiating a subject with radiation to photograph a moving state of the subject. The program causes the computer to achieve functions of acquiring a plurality of frame images constituting the kinetic image; generating a first image which is a synthesized still image obtained by synthesizing at least two or more frame images among the plurality of frame images; and outputting the first image to an output unit. Before generating the first image, the function of outputting the first image to the output unit outputs a second image which is a still image based on at least one or more frame images among the plurality of frame images and has an image quality lower than an image quality of the first image.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF THE EMBODIMENTS

Hereinafter, embodiments of the present invention will be described with reference to the drawings. However, the scope of the invention is not limited to the illustrated examples.

First Embodiment

Configuration of Image Processing System 100

A configuration of a first embodiment will be described first.

Figure 1:
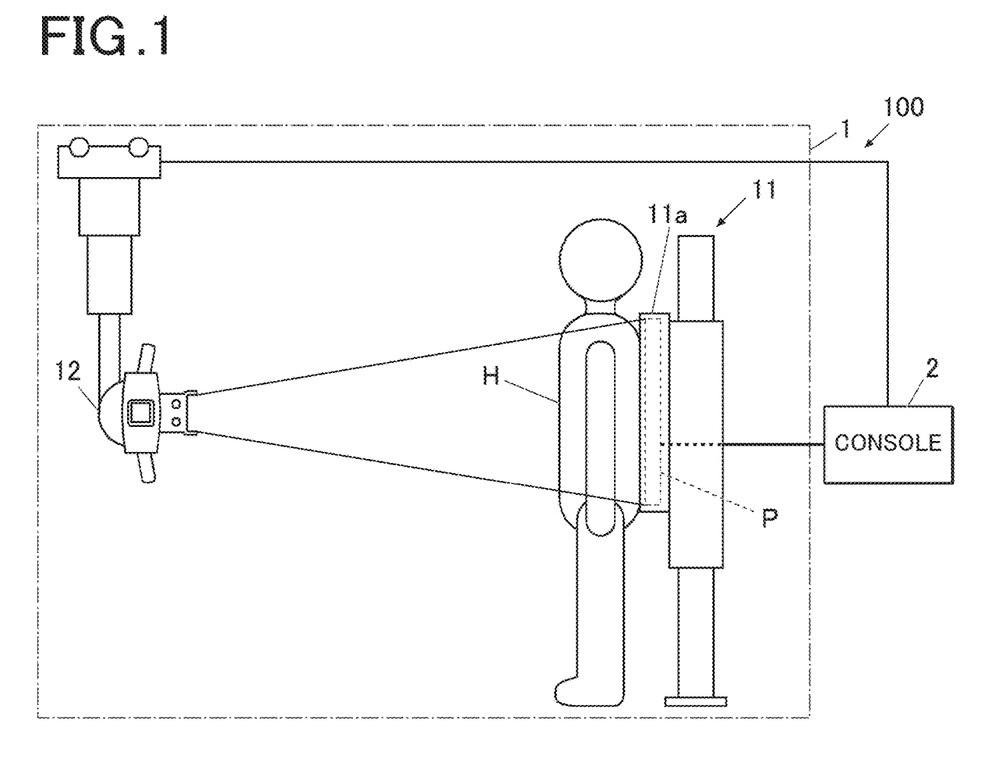
FIG. 1 is a diagram showing an overall configuration of an image processing system in an embodiment of the present invention.

FIG. 1 is a diagram showing an overall configuration example of an image processing system 100 according to the present embodiment. As shown in FIG. 1, the image processing system 100 includes a photographing device 1 and a console 2 connected to each other to be able to transmit/receive data to/from each other.

The photographing device 1 is a photographing device that irradiates a subject with radiation to perform still image photography or kymography. In the present embodiment, the kymography is performed using, as the subject, a diagnosis target region of a human body having periodicity (a cycle) such as morphological changes of lung expansion and contraction associated with a respiratory motion or heartbeat, for example. A series of images obtained by continuously photographing the subject by kymography will be referred to as a kinetic image. Each of a plurality of images constituting the kinetic image will be referred to as a frame image.

The kymography includes videography, but not include photographing a still image while displaying video.

The kinetic image includes video, but not include an image obtained by photographing a still image while displaying video.

The photographing device 1 includes a radiation detector P, a photographing table 11 in which the radiation detector P is to be loaded, and a radiation generation device 12. The radiation detector P is loaded in a holder 11a of the photographing table 11.

The radiation detector P is implemented by a semiconductor image sensor such as a flat panel detector (FPD) and is provided opposite to the radiation generation device 12 with a subject H interposed therebetween. The radiation detector P has a glass substrate and the like, for example, and includes a plurality of detection elements (pixels) arranged in a matrix form at a predetermined position on the substrate. The detection elements each detect radiation (an X-ray) emitted from the radiation generation device 12 and transmitted through at least the subject H in accordance with the intensity of the radiation and convert the detected radiation to an electric signal and accumulate the electric signal. Each pixel includes a switching element such as a thin film transistor (TFT), for example. The radiation detector P controls the switching element of each pixel based on image reading conditions input from the console 2, switches reading of the electric signal accumulated in each pixel, and reads the electric signal accumulated in each pixel, thereby acquiring an image as image data. Then, the radiation detector P outputs the acquired image data to the console 2.

The radiation generation device 12 is arranged at a position opposite to the radiation detector P with the subject H interposed therebetween and irradiates the radiation detector P loaded in the holder 11a with the radiation via a patient as the subject H based on radiation irradiation conditions input from the console 2, thereby performing photography.

The console 2 outputs photographing conditions such as the radiation irradiation conditions and the image reading conditions to the photographing device 1 to function as an image processing apparatus that controls radiography and a reading operation of a radiation image (an image) performed by the photographing device 1, and also subjects the images acquired by the photographing device 1 to image processing.

Figure 2:
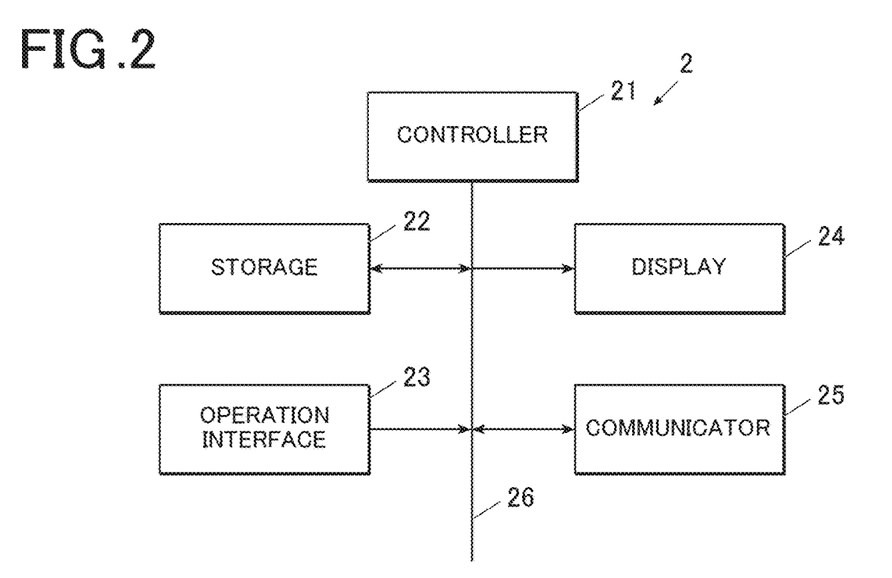
FIG. 2 is a block diagram showing a functional configuration of a console of FIG. 1.

As shown in FIG. 2, the console 2 includes a controller 21, a storage 22, an operation interface 23, a display 24, and a communicator 25, and the respective units are connected via a bus 26.

The controller 21 includes a central processing unit (CPU), a random access memory (RAM), and the like. The CPU of the controller 21 reads a system program and various processing programs stored in the storage 22 in response to an operation of the operation interface 23, develops the programs in the RAM, and controls an operation of each unit of the console 2, and the radiation irradiating operation and the reading operation of the photographing device 1 in a centralized manner according to the developed programs. The controller 21 also executes various processes including a synthesized still image generation process A and the like which will be described later using a plain photographed image or kinetic image transmitted from the radiation detector P of the photographing device 1, and functions as an acquisition unit, a generator, and an output controller.

An overview of a synthesized still image generation process will be described below with reference to FIG. 3 and FIG. 4.

Figure 3:
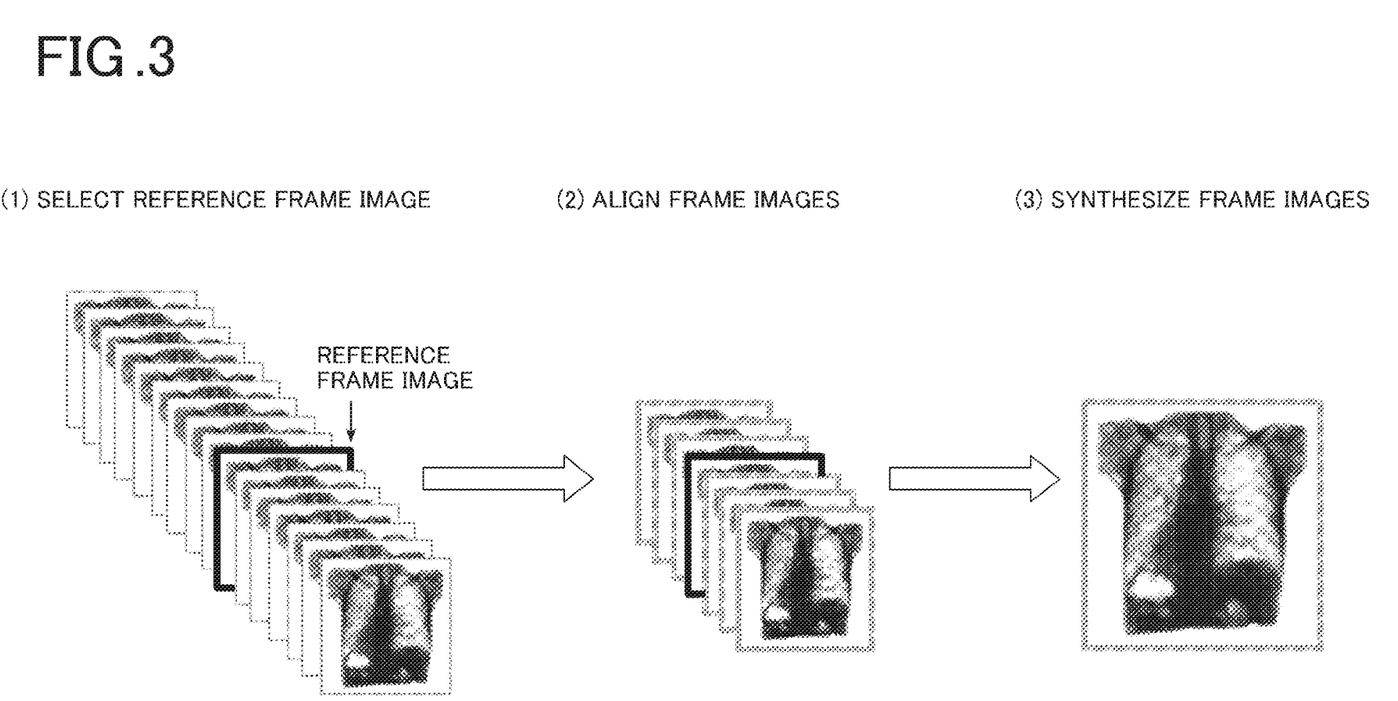
FIG. 3 is a diagram showing an overview of a synthesized still image generation process.

FIG. 3 shows an overview of the synthesized still image generation process. The synthesized still image generation process is a process of generating a still image that enables a morphological diagnosis from a kinetic image. A synthesized still image refers to a still image obtained by synthesizing frame images.

First, the controller 21 selects a reference frame image from among a plurality of frame images of a kinetic image. This reference frame image may be selected either automatically or manually.

In the case of automatic selection, the reference frame image may be determined based on a feature amount calculated by analyzing each of the plurality of frame images by the controller 21 of the console 2, as in the conventional technology of JP 2019-212138 A, for example.

In the example of FIG. 3, a frame image indicated by a thick frame and an arrow is used as the reference frame image.

Next, the controller 21 aligns frame images targeted for synthesizing processing. FIG. 3 shows an example in which the controller 21 determines three frame images preceding and three frame images succeeding the reference frame image as frame images targeted for synthesizing processing and aligns the frame images targeted for synthesizing processing on the reference frame image.

Finally, the controller 21 synthesizes the aligned frame images, and finishes the synthesized still image generation process. Examples of a method of synthesizing a plurality of frame images include a method of taking an average value from pixels located at spatially the same position. By performing the synthesized still image generation process, a still image that achieves a graininess improving effect as compared with a single frame image and has an image quality equivalent to that of a plain photographed image is generated. In other words, it is not necessary to additionally perform plain photography after kymography, so that reduction of an exposure dose of a patient and improvement in work flow of a photographer are expected.

The image quality includes at least one of resolution, definition, graininess, and sharpness. Examples of factors that affect the "image quality" include the number and resolution of frame images targeted for synthesis, and the alignment accuracy between the frame images targeted for synthesis.

The alignment accuracy depends on settings of a coordinate transformation algorithm, a similarity evaluation function of evaluating whether an image after transformation conforms with a goal image which will be described later, a pixel block size to be referred to in similarity evaluation, an image resolution level, and the like. To cite an example with respect to the image resolution level among them, a result of alignment differs depending on whether alignment is performed with images left at the same size (high resolution) or alignment is performed after reducing images once to a low resolution. In the former case, alignment is performed in a narrow range while referring to original pixels one by one. Thus, alignment in a narrow area is given priority, and the alignment accuracy for fine structures such as blood vessels increases. In the latter case, alignment is performed upon sub-sampling pixels along with the reduction. Thus, alignment in a wide area is given priority, and the alignment accuracy for large structures such as ribs and the diaphragm increases. In general, in alignment at a plurality of resolutions, rough alignment is initially performed at a low resolution, and then alignment at a high resolution is performed. Highly-accurate alignment is thereby achieved both in a wide area and a narrow area. At this time, in a case in which a plurality of frame images are synthesized in a state where only low-resolution images have been aligned, fine structures such as blood vessels not having been aligned in a synthesized still image are brought into a state reduced in sharpness.

Figure 4:
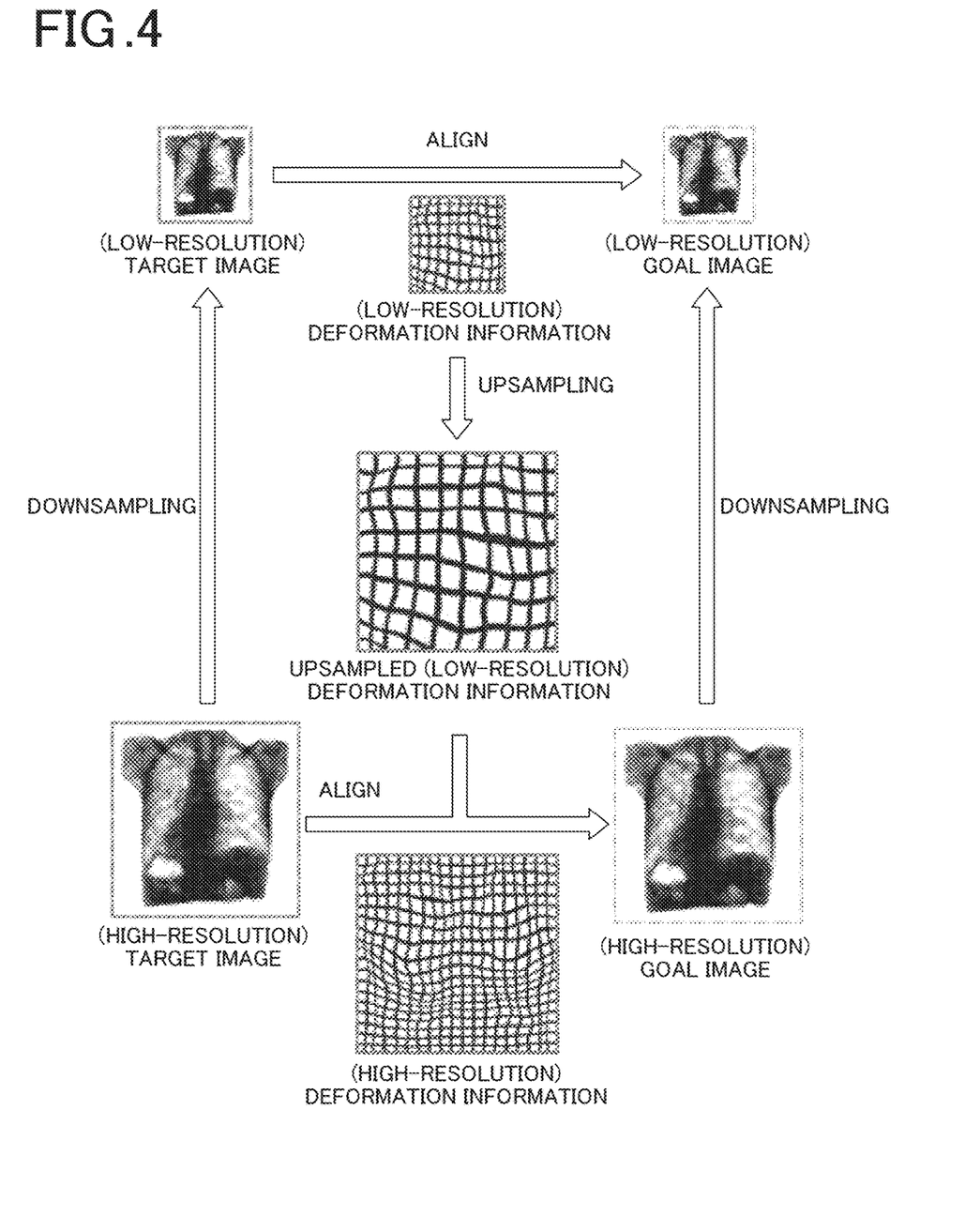
FIG. 4 is a diagram showing an overview of processing of aligning frame images targeted for synthesizing processing.

FIG. 4 is an overview of processing of aligning frame images targeted for synthesizing processing in the synthesized still image generation process. FIG. 4 shows alignment of two images as an example. Alignment processing which will be described later is in the form in which alignment at a plurality of resolutions is performed in sequence from a low resolution to a high resolution, while the present embodiment shows an example of performing alignment in two steps.

A goal image is an image to be a goal of alignment, which specifically is a reference frame image.

A target image is an image to be subjected to coordinate transformation by alignment, which specifically is a frame image targeted for synthesizing processing.

Deformation information is information to be used for alignment, which specifically is information to be used for coordinate transformation.

First, the controller 21 downsamples a target image and a goal image. The controller 21 obtains a target image and a goal image reduced in resolution by downsampling.

Next, the controller 21 aligns the target image and the goal image at the low resolution. The controller 21 obtains (low-resolution) deformation information to be used for coordinate transformation of the target image.

Next, the controller 21 upsamples the (low-resolution) deformation information. The controller 21 obtains deformation information obtained by upsampling the (low-resolution) deformation information. By upsampling the (low-resolution) deformation information, the controller 21 can use the upsampled deformation information as initial deformation information when aligning the target image and the goal image at the high resolution.

Next, the controller 21 aligns the target image and the goal image at the high resolution using the upsampled deformation information as the initial deformation information and finishes alignment processing. The controller 21 obtains (high-resolution) deformation information.

FIG. 4 shows alignment of two images as an example, while the alignment processing shown in FIG. 4 is repeatedly performed in a case in which there are a plurality of frame images targeted for synthesizing processing.

The foregoing has described an overview of the synthesized still image generation process.

The storage 22 is implemented by a nonvolatile semiconductor memory, hard disk, or the like. The storage 22 stores various programs to be executed by the controller 21, parameters required for the execution of processing by the programs, or data such as processing results. Each program is stored in the form of a readable program code, and the controller 21 successively executes an operation according to the program code.

The storage 22 also stores the photographing conditions (the radiation irradiation conditions and the image reading conditions) corresponding to photographing regions. The storage 22 further stores photographing order information transmitted from a radiology information system (RIS) not shown or the like. The photographing order information includes information such as patient information and inspection information (such as an inspection ID, a photographing region (also including a photographing direction), an inspection date, and the type indicating still image photography or videography).

The storage 22 also stores a plain photographed image and kinetic image having been photographed as well as images generated by image processing, in association with the patient information and the inspection information.

The operation interface 23 includes a keyboard having a cursor key, numeric input keys, various function keys, and the like, and a pointing device such as a mouse, and outputs, to the controller 21, an instruction signal input by a key operation to the keyboard, or a mouse operation. The operation interface 23 may also include a touch panel on a display screen of the display 24. In this case, the instruction signal input via the touch panel is output to the controller 21. The operation interface 23 further includes an exposure switch to instruct kymography to the radiation generation device 12.

The display 24 is implemented by a monitor such as a liquid crystal display (LCD) or a cathode ray tube (CRT), and displays an input instruction, data, or the like from the operation interface 23 in accordance with an instruction of a display signal input from the controller 21, and functions as an output unit.

The communicator 25 has an interface for transmitting/receiving data to/from the radiation generation device 12 and the radiation detector P. Communication of the console 2 with the radiation generation device 12 and the radiation detector P may be wired communication or wireless communication.

The communicator 25 includes a LAN adaptor, a modem, a terminal adapter (TA), and the like, and controls data transmission/reception to/from the RIS or the like not shown but connected to a communication network.

Operation of Image Processing System 100

When the photographing order information on a photographing target is selected by the operation interface 23 in the console 2 in a state in which the radiation detector P has been set in the holder 11a in the photographing device 1, the photographing conditions (the radiation irradiation conditions and the radiation image reading conditions) corresponding to the selected photographing order information are read from the storage 22, transmitted to the photographing device 1, and set in the photographing device 1. When the subject H is positioned and the exposure switch is depressed, the subject is irradiated with radiation by the radiation generation device 12 in the photographing device 1, and a plain photographed image or a plurality of frame images constituting a kinetic image are acquired by the radiation detector P and transmitted to the console 2.

In the console 2, the controller 21 functions as an acquisition unit. Upon acquisition of a plain photographed image or a plurality of frame images constituting a kinetic image from the radiation detector P via the communicator 25, the controller 21 causes the acquired plain photographed image or plurality of frame images constituting a kinetic image to be stored in the storage 22 in association with the patient information and the inspection information. The controller 21 executes the synthesized still image generation process A based on the acquired kinetic image.

Figure 5:
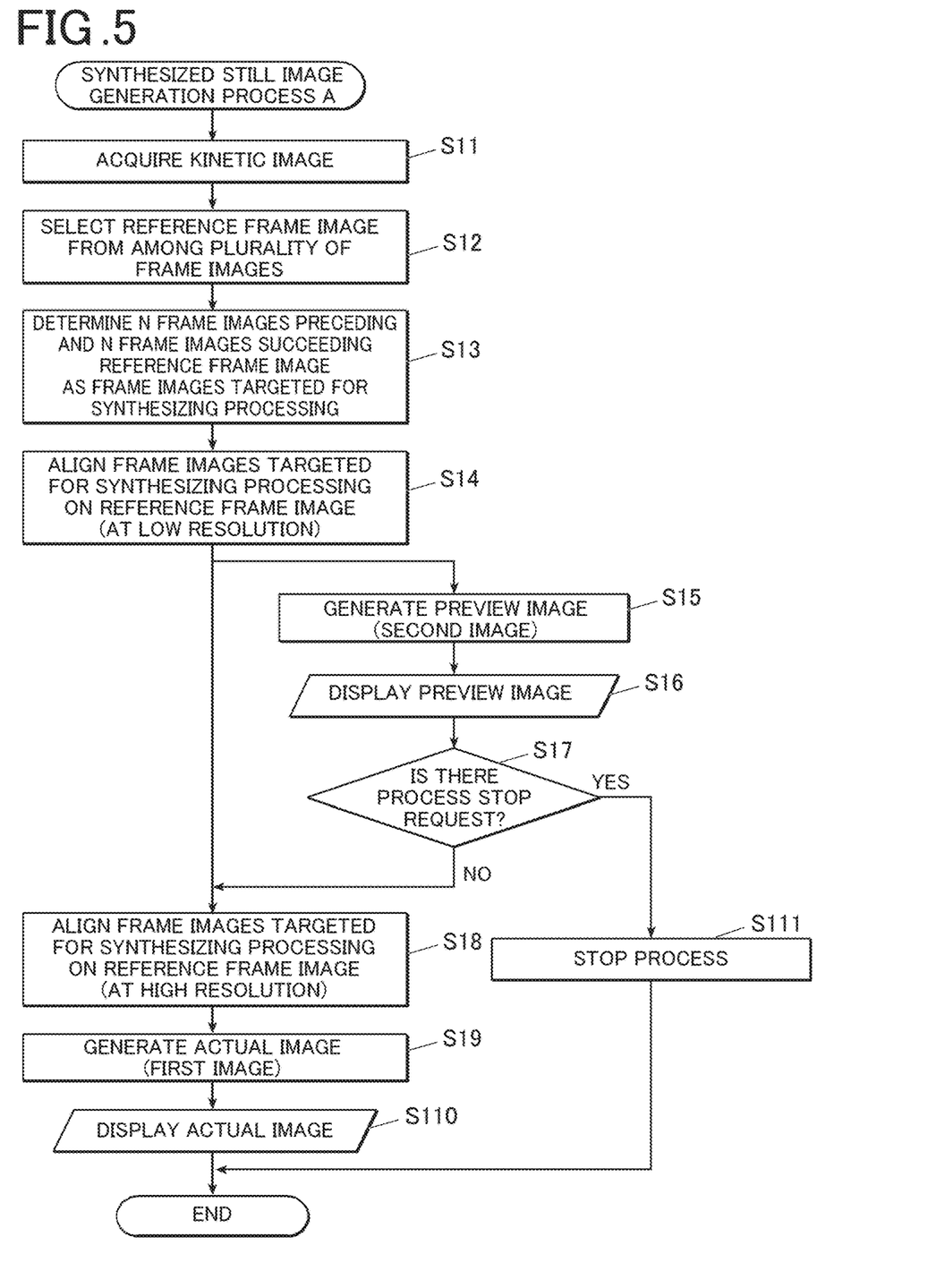
FIG. 5 is a flowchart showing a flow of a synthesized still image generation process A to be executed by a controller of FIG. 2 in a first embodiment.

FIG. 5 is a flowchart showing a flow of the synthesized still image generation process A. The synthesized still image generation process A is executed by cooperation between the controller 21 and a program stored in the storage 22.

First, the controller 21 acquires a kinetic image including a plurality of frame images via the communicator 25 (step S11).

Next, the controller 21 selects a reference frame image from among the plurality of frame images (step S12). The reference frame image may be selected either automatically or manually as described earlier.

Next, the controller 21 determines N frame images preceding and N frame images succeeding the reference frame image as frame images targeted for synthesizing processing (step S13). The number of frames (N) may be set in advance before the synthesized still image generation process A is started or may be set after the synthesized still image generation process A is started.

In the case of setting the number of frames (N) after the synthesized still image generation process A is started, a method of setting the number of frames (N) depending on the degree of movement in frame images preceding and succeeding the reference frame image is cited, for example. Specifically, in a case in which the body movement is large and there are many preceding and succeeding frames less correlated to the reference frame image, the number of frames (N) is set small. In contrast, in a case in which there are many preceding and succeeding frames highly correlated to the reference frame image, the number of frames (N) is set larger.

Next, the controller 21 aligns all of the frame images targeted for synthesizing processing (the preceding N frames and succeeding N frames) on the reference frame image at the low resolution (step S14). Specifically, low-resolution frame images obtained by reducing the resolution of the acquired frame images are aligned to obtain deformation information a which is information to be used for coordinate transformation.

The alignment at the low resolution is processed at a higher speed than the alignment at the high resolution since the number of pixels to be subjected to alignment processing is smaller.

When the alignment at the low resolution is finished, the controller 21 functions as a generator to subject the frame images (the preceding N frames and succeeding N frames) to coordinate transformation using the deformation information a obtained in step S14 and synthesize the reference frame image and the frame images targeted for synthesizing processing (the preceding N frames and succeeding N frames) to generate a preview image (a second image) (step S15).

Next, the controller 21 causes the display 24 that functions as the output unit to display the preview image (step S16). Together with the preview image, confirmation items are also displayed. The confirmation items refer to whether the reference frame image is correct, and an image noise reduction effect, for example.

The image quality of the preview image is lower than the image quality of an actual image (a first image) which will be described later.

In the case of synthesizing the frame images using the deformation information a, the preview image has a low resolution. However, if the frame images are synthesized in step S15 using deformation information b obtained by upsampling the deformation information a, the resolution of the preview image will be the same as that of the actual image which will be described later.

In a case in which the controller 21 fails in generating the preview image or the quality of the preview image generated by the controller 21 does not satisfy a specific standard, the controller 21 may output alarm information on the display 24. This enables a user to immediately recognize an obvious problem, if any, in the preview image.

Next, the user confirms the preview image, and if there is any problem, sends a process stop request to the controller 21 using the operation interface 23 (step S17). Then, the controller 21 stops alignment in step S18 which will be described later (step S111). In a case in which the process is stopped, the synthesized still image generation process A is finished.

In parallel to generation of the preview image in step S15, processing of generating an actual image (step S18, step S19) is started. First, the controller 21 aligns the frame images targeted for synthesizing processing on the reference frame image at a high resolution (step S18). In the alignment, new deformation information c is obtained using, as the initial deformation information, the deformation information b obtained by upsampling the deformation information a obtained in step S14.

If the upsampled deformation information b has been obtained in step S15, the deformation information b is used as the initial deformation information.

Next, when the alignment at the high resolution is finished, the controller 21 functions as the generator to subject frame images (the preceding N frames and succeeding N frames) to coordinate transformation using the deformation information c obtained in step S18 and synthesize the reference frame image and the frame images targeted for synthesizing processing (the preceding N frames and succeeding N frames) to generate an actual image (the first image) (step S19).

Next, the controller 21 causes the display 24 that functions as the output unit to display the actual image (step S110), and finishes the synthesized still image generation process A.

The actual image generated by the synthesized still image generation process A is stored in the storage 22 in association with the patient information and the inspection information on the original kinetic image.

In this manner, the alignment at the low resolution is processed at a higher speed than the alignment at the high resolution. Thus, by generating a synthesized still image for preview once at a point of time when the alignment at the low resolution is completed, and previously displaying the synthesized still image for preview on the console, the user is able to promptly confirm whether the reference frame image is correct and the image noise reduction effect.

Second Embodiment

Hereinafter, a second embodiment of the present invention will be described. In the first embodiment, the controller 21 aligns all of the frame images targeted for synthesizing processing (the preceding N frames and succeeding N frames) at the low resolution, once displays a preview image, then performs the alignment processing at the high resolution, and displays an actual image.

In the second embodiment, the controller 21 aligns a certain number of frame images (preceding n frames and succeeding n frames where n<N) among frame images targeted for synthesizing processing, displays a preview image, then aligns the remaining (N-n) frame images targeted for synthesizing processing, and displays an actual image.

In the second embodiment, a program for executing a synthesized still image generation process B which will be described later is stored in the storage 22.

The remaining configuration in the second embodiment is similar to the configuration described in the first embodiment with reference to FIG. 1 and FIG. 2, and description is therefore omitted. An operation of the image processing system 100 in the second embodiment is similar to the operation in the first embodiment with respect to the photographing device 1, and description is therefore omitted. Hereinafter, the synthesized still image generation process B to be executed in the console 2 based on a kinetic image acquired from the photographing device 1 will be described.

Figure 6:
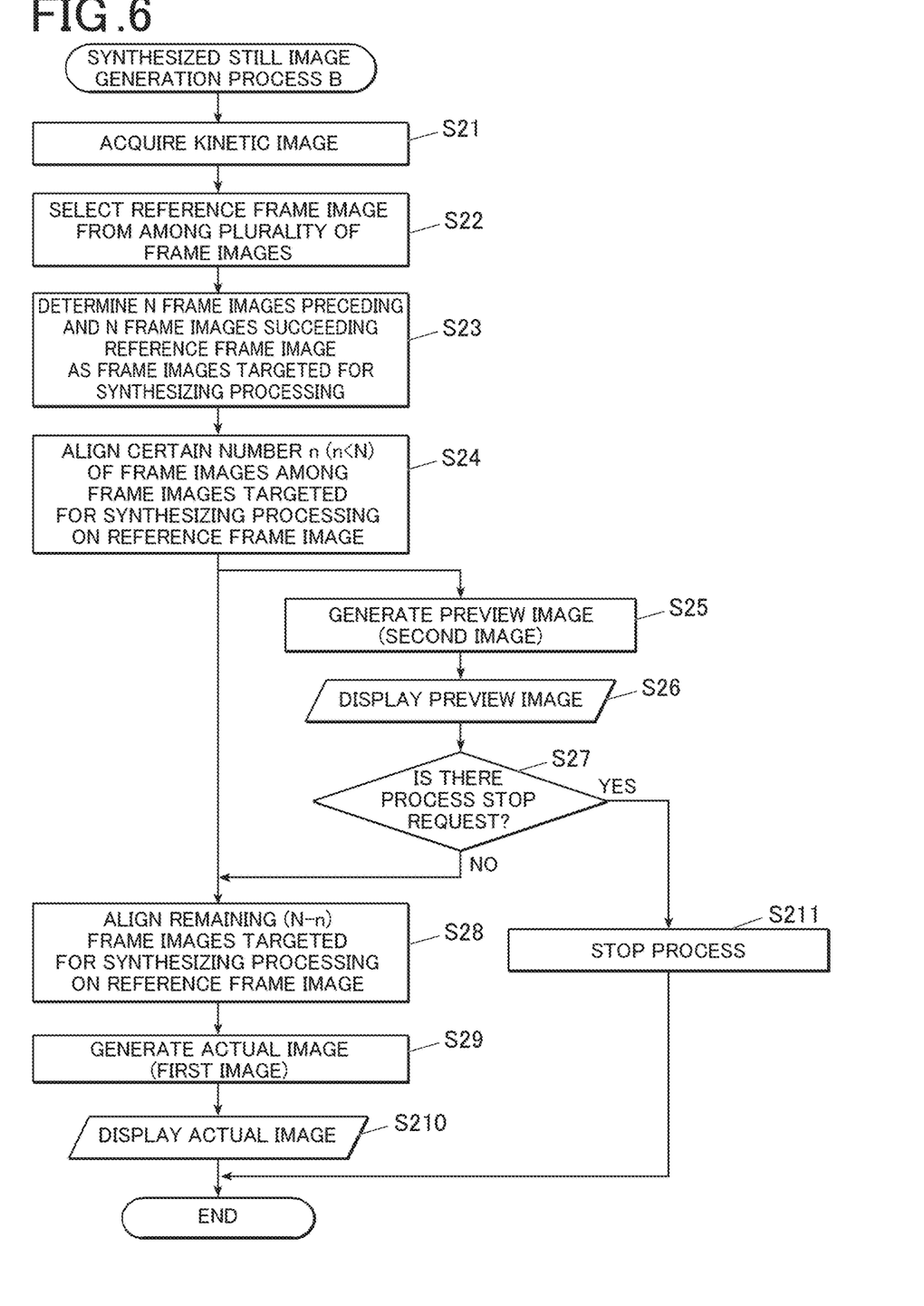
FIG. 6 is a flowchart showing a flow of a synthesized still image generation process B to be executed by the controller of FIG. 2 in a second embodiment.

FIG. 6 is a flowchart showing a flow of the synthesized still image generation process B. The synthesized still image generation process B is executed by cooperation between the controller 21 and the program stored in the storage 22.

In FIG. 6, step S21 to step S23 are similar to step S11 to step S13 of FIG. 5, and description is therefore omitted.

In the synthesized still image generation process B, alignment which will be described later may be alignment at a plurality of resolutions.

The controller 21 aligns a certain number of frame images (the preceding n frames and succeeding n frames) among frame images targeted for synthesizing processing on a reference frame image (step S24). Specifically, the controller 21 aligns a certain number of frame images among acquired frame images and obtains deformation information d which is information to be used for coordinate transformation.

Since the alignment of the certain number of frame images (the preceding n frames and succeeding n frames) is processed at a high speed since the number of frame images (n<N) is smaller than when aligning all of frame images (the preceding N frames and succeeding N frames).

The number of frames (n) may be set in advance before the synthesized still image generation process B is started or may be set after the synthesized still image generation process B is started. The example of setting the number of frames (n) after the synthesized still image generation process B is started is the same as the aforementioned example of the synthesized still image generation process A.

Next, when the alignment of the certain number of frame images is finished, the controller 21 functions as the generator to subject the frame images (the preceding n frames and succeeding n frames) to coordinate transformation using the deformation information d obtained in step S24, and synthesize the reference frame image and the frame images targeted for synthesizing processing (the preceding n frames and succeeding n frames), thereby generating a preview image (the second image) (step S25).

Next, the controller 21 causes the display 24 that functions as the output unit to display the preview image (step S26).

Next, the user confirms the preview image, and if there is any problem, sends a process stop request to the controller 21 using the operation interface 23 (step S27). Then, the controller 21 stops alignment of step S28 which will be described later (step S211). In a case in which the process is stopped, the synthesized still image generation process B is finished.

In parallel to generation of the preview image in step S25, processing of generating an actual image (step S28, step S29) is started. First, the controller 21 aligns, on the reference frame image, the remaining (N-n) frame images targeted for synthesizing processing other than the certain number of frame images targeted for synthesizing processing among the frame images targeted for synthesizing processing (step S28). In the alignment, deformation information e is obtained.

Next, when alignment of all of the frame images targeted for synthesizing processing is finished, the controller 21 functions as the generator to perform coordinate transformation using the deformation information d obtained in step S24 and the deformation information e obtained in step S28 and synthesize the reference frame image and the frame images targeted for synthesizing processing, thereby generating an actual image (the first image) (step S29).

Next, the controller 21 causes the display 24 that functions as the output unit to display the actual image (step S210), and finishes the synthesized still image generation process B.

A synthesized still image generated by the synthesized still image generation process B is stored in the storage 22 in association with the patient information and the inspection information on the original kinetic image.

In this manner, a smaller number of frame images are aligned at a higher speed than when aligning all of the frame images targeted for synthesizing processing. Thus, by once generating a synthesized still image for preview at a point of time when the alignment of a smaller number of frame images is completed and previously displaying the synthesized still image for preview on the console, the user is able to promptly confirm whether the reference frame image is correct and degradation in image quality that would occur in a case in which alignment of a small number of frames fails under the influence of a body movement.

If degradation in image quality that would occur in the case in which alignment of a small number of frames fails under the influence of a body movement is confirmed, a high image quality is unlikely to be secured if the remaining (N-n) frames are synthesized. Thus, if there is any problem in the preview image, the process is interrupted at that point of time in order to determine reprocessing or rephotographing.

As described above, the image processing apparatus (the console 2) that processes a kinetic image obtained by kymography of irradiating a subject with radiation to photograph a moving state of the subject includes an acquisition unit (the controller 21) that acquires a plurality of frame images constituting a kinetic image, a generator (the controller 21) that generates a first image which is a synthesized still image obtained by synthesizing at least two or more frame images among the plurality of frame images, and an output controller (the controller 21) that outputs the first image to the output unit. Before generating the first image, the output controller outputs a second image which is a still image based on at least one or more frame images among the plurality of frame images and has an image quality lower than an image quality of the first image. This enables the user to promptly determine whether reprocessing or rephotographing is necessary by confirming the second image.

This enables stress on the user and a wasted waiting time to be reduced when generating a synthesized still image from a plurality of frame images constituting a kinetic image.

The description in the above embodiments is a preferred example of the present invention, and the present invention is not limited to this example.

For example, in the embodiment in which alignment at a plurality of resolutions is performed in sequence from a low resolution to a high resolution, there may be more than two steps of the low resolution and the high resolution.

A flow of alignment in this case will be described. As a specific example, alignment of two frame images will be described. First, low-resolution frame images obtained by reducing the resolution of acquired frame images are aligned to obtain the deformation information a which is information to be used for coordinate transformation. Next, frame images increased in resolution are aligned using the deformation information b obtained by upsampling the deformation information a as initial deformation information to obtain the new deformation information c. Next, frame images further increased in resolution are aligned using the deformation information d obtained by upsampling the deformation information c as initial deformation information to obtain the new deformation information e.

In other words, alignment at a higher resolution is repeatedly performed using deformation information obtained by alignment at a lower resolution as a starting point (initial deformation information). For example, alignment is performed while gradually increasing the resolution in an order such as ⅛, ¼, ½, and the same size.

Additionally, in the case of the embodiment in which alignment at a plurality of resolutions is performed in sequence from a low resolution to a high resolution, a synthesized still image may be generated at a point of time when alignment at each resolution is finished, and the synthesized still image may be reflected sequentially in the second image. In this case, the user is able to confirm the synthesized image at each resolution.

Timing of preview display is settable. For example, preview display is performed at timing when alignment at the resolution of ¼ is completed.

A preview image may be displayed a plurality of times. For example, preview display is performed at timing when alignment at the resolutions of ⅛ and ½ is completed.

The respective magnifications and steps of the gradually-increased resolutions are settable.

While a preview image or an actual image is being displayed on the display 24, an icon or a comment indicating that the preview image or the actual image is being displayed may be displayed on the display 24.

While step S18 and step S19 or step S28 and step S29 executed in parallel to step S15 or step S25 are being executed, the degree of progress may be displayed on the display 24. Examples thereof include displaying a comment indicating that 50% is completed, displaying the degree of progress on a horizontal axis with the maximum value set at 100%, and the like.

It may be configured such that, while a preview image is being displayed on the display 24, image adjustment, image processing (gradation processing), and the like are not allowed to be operated. Image adjustment, image processing (gradation processing), and the like are allowed to be operated while an actual image is being displayed on the display 24.

In step S16 of the first embodiment or step S26 of the second embodiment, the reference frame image may be displayed as a preview image. In this case, the flow is branched immediately after step S12 or step S22, and the processing of generating an actual image (steps S13-S14 and step S18-S19, steps S23-S24 and steps S28-S29) and the processing of generating a preview image (steps S15-S17, steps S25-S27) are executed in parallel. This enables a user to confirm the reference frame image as a preview image sooner to promptly confirm whether the reference frame image is correct.

The actual image is generated based on the reference frame image and at least one frame image other than the reference frame image and displayed.

When generating the preview image, at least one frame image among frame images used for generating the actual image is used.

The configuration of generating a preview image is not limited to the generator (the controller 21) of the image processing apparatus (the console 2) but may be a processing apparatus other than the image processing apparatus (the console 2), a server, or the like, for example.

For example, the above description discloses an example in which a hard disk, semiconductor nonvolatile memory, or the like is used as a computer-readable medium for a program according to the present invention, but the present invention is not limited to this example. As another computer-readable medium, a portable recording medium such as a CD-ROM can be applied. Carrier waves are also applied as a medium for providing data on the program according to the present invention via a communication line.

Additionally, a detailed configuration and a detailed operation of each apparatus that constitutes the image processing system can be appropriately changed within the scope of claims of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent application No. 2021-098460, filed on Jun. 14, 2021, is incorporated herein by reference in its entirety.

What is claimed is:

1. An image processing apparatus that processes a kinetic image obtained by kymography of irradiating a subject with radiation to photograph a moving state of the subject, the image processing apparatus comprising:
    an acquisition unit that acquires a plurality of frame images constituting the kinetic image,
    a generator that generates a first image which is a synthesized still image obtained by synthesizing at least two or more frame images among the plurality of frame images; and
    an output controller that outputs the first image to an output unit, wherein
    before generating the first image, the output controller outputs a second image which is a still image based on at least one or more frame images among the plurality of frame images and has an image quality lower than an image quality of the first image,
    wherein the generator generates, as the second image, a synthesized still image obtained by synthesizing at least two or more frame images among the plurality of frame images, and
    the generator performs alignment at a plurality of resolutions in sequence from a low resolution to a high resolution a plurality of times, and generates, as the second image, a synthesized still image at a point of time when alignment at each of the resolutions is finished.

2. The image processing apparatus according to claim 1, wherein the second image is a synthesized still image obtained by synthesizing at least two or more frame images among the plurality of frame images.

3. The image processing apparatus according to claim 2, wherein the second image is generated under a condition that an alignment accuracy during synthesis is lower than the first image.

4. The image processing apparatus according to claim 1, wherein the second image is generated from a smaller number of frame images than the first image.

5. The image processing apparatus according to claim 1, wherein the generator starts alignment at a subsequent resolution while generating the second image.

6. The image processing apparatus according to claim 1, wherein the generator generates the first image using information obtained when generating the second image.

7. The image processing apparatus according to claim 1, wherein the output controller outputs alarm information to the output unit in a case in which the generator fails in generating the second image, or in a case in which a quality of information on the second image generated by the generator does not satisfy a specific standard.

8. The image processing apparatus according to claim 1, wherein
the generator generates the first image based on a reference frame image among the plurality of frame images and at least one frame image other than the reference frame image, and
the second image is the reference frame image.

9. The image processing apparatus according to claim 1, wherein the generator generates the second image using at least one frame image among the frame images used for generating the first image.

10. The image processing apparatus according to claim 1, wherein the image quality includes at least one of resolution, definition, graininess, and sharpness.

11. A non-transitory recording medium having stored thereon a program for a computer to be used in an image processing apparatus that processes a kinetic image obtained by kymography of irradiating a subject with radiation to photograph a moving state of the subject, the program causing the computer to achieve functions of:
acquiring a plurality of frame images constituting the kinetic image,
generating a first image which is a synthesized still image obtained by synthesizing at least two or more frame images among the plurality of frame images; and
outputting the first image to an output unit, wherein
before generating the first image, the function of outputting the first image to the output unit outputs a second image which is a still image based on at least one or more frame images among the plurality of frame images and has an image quality lower than an image quality of the first image,
wherein the method further comprises generating, as the second image, a synthesized still image obtained by synthesizing at least two or more frame images among the plurality of frame images, and
performing alignment at a plurality of resolutions in sequence from a low resolution to a high resolution a plurality of times, and generating, as the second image, a synthesized still image at a point of time when alignment at each of the resolutions is finished.

* * * * *